United States Patent [19]

Gerhard

[11] Patent Number: 4,689,308
[45] Date of Patent: Aug. 25, 1987

[54] ARTICLE FOR PREPARING A CHEMICAL SENSOR FOR USE

[75] Inventor: Gregory J. Gerhard, Seattle, Wash.

[73] Assignee: International Biomedics, Inc., Bothell, Wash.

[21] Appl. No.: 858,391

[22] Filed: May 1, 1986

[51] Int. Cl.⁴ .......................................... G01N 31/00
[52] U.S. Cl. ..................................... 436/18; 436/19; 436/8
[58] Field of Search ..................... 436/8–19, 436/2; 204/403, 427, 428, 433, 422; 128/635; 422/98; 222/143, 522, 524

[56] References Cited

U.S. PATENT DOCUMENTS

| 1,680,616 | 8/1928 | Horst | 436/8 |
| 3,060,130 | 10/1962 | Sacks | 436/8 |
| 4,399,022 | 8/1983 | Nakajima et al. | 436/19 |

Primary Examiner—Deborah L. Kyle
Assistant Examiner—T. J. Wallen
Attorney, Agent, or Firm—Graybeal, Jensen & Puntigam

[57] ABSTRACT

The article includes a first vial (12) which is positioned within a second larger vial (32). The first vial (12) separately contains a first fluid, such as a first calibrating fluid, and the second vial (32) contains a second fluid, such as a second calibrating fluid. A stopper (18) seals the first vial (12) and holds a sensing portion (21) of the sensor in the first vial (12). The first vial (12) is released from the second vial (32) by activating a plunger (36).

An encapsulation package (50) having first and second elements (51, 52) maintains the chemical sensor and a calibrating article or vessel in a sterile condition. The package includes a first cavity (54) which receives the calibrating vessel, the sensing portion of the sensor and a substantial portion of the sensor cable, and a second cavity (56) which receives the sensor connector. A passageway (58) connecting the two cavities (54, 56) is adapted to receive a portion of the sensor cable.

13 Claims, 5 Drawing Figures

ARTICLE FOR PREPARING A CHEMICAL SENSOR FOR USE

DESCRIPTION

1. Technical Field

This invention relates generally to a system for selectively mixing at least two segregated fluids, typically for the purpose of preparing a chemical sensor for use, such as calibration of such a sensor with calibrating fluids with two different values.

2. Background Art

There are many situations which require the selective mixing of two or more fluids, and it is often desirable that the fluids be maintained segregated within a single system or arrangement until mixing is to be effected.

One example is the combining of certain polymers and their initiators, which are hazardous to handle separately. Another example is the calibration of chemical sensors, such as a pH sensor, which is used for fetal monitoring. With such sensors, it is sometimes necessary that calibration be accomplished at two operating points, because the operating response of such sensors is sometimes irregular. Previously, such calibration has typically been accomplished with two separate vessels containing the desired calibration buffers. A trained technician calibrates the sensor using first one calibration buffer and then the other.

A single, two compartment vessel containing two fluids for use in such circumstances is known, with the compartments being divided by a breakable wall. Mixing of the fluids in the separated compartments is accomplished by breaking the dividing wall. Such a system is generally not desirable, however, because it is cumbersome and because the breaking of a dividing wall to achieve the desired mixing has inherent disadvantages.

In the calibration of chemical sensors it is also often very important to maintain the sterility of the sensor, both during calibration and from then up to the time of actual use. Sometimes it is difficult for the technician to maintain sensor sterility using two separate calibration vessels. Calibration of a sensor is even more difficult when a portion of the connecting sensor cable, in addition to the actual sensing portion of the sensor, must also be maintained in a sterile condition during calibration.

Chemical sensors of the type above mentioned, such as a pH sensor, frequently must also have the sensing portion thereof continuously hydrated during shipment and storage prior to actual use. The sensor cable, however, should be kept dry. Further, the sensor must usually be packaged so that it can survive shipment and subsequent handling and storage without compromise to sterility. Still further, many sensors must be capable of being heated to a specific temperature, such as body temperature, within a short period of time without compromising sterility.

DISCLOSURE OF THE INVENTION

Accordingly, the present invention is an article of manufacture which includes at least two separate vials for holding two fluids arranged to permit convenient selective mixing thereof. The article is referred to as a mixing vessel.

The first vial includes a stopper means which seals the first vial and holds the sensing portion of the sensor in the first fluid, such as a first calibration buffer. The first vial and the stopper are combined with a second vial which contains the second fluid, such as a second calibration buffer. The stopper means also seals the second vial. Means are provided for separating the first vial from the stopper, which in turn results in the mixing of the first and second buffers.

Encapsulation means for the combination of the mixing vessel and the sensor is also provided. The encapsulation means is a package having upper and lower elements, the lower element having a first cavity for receiving the mixing vessel, the sensing portion of the sensor and a substantial portion of the sensor cable, a second cavity for receiving the connector portion of the sensor, and a passage connecting the two cavities for receiving a portion of the sensor cable. The upper element is removably sealed to the lower element around the peripheries of the first and second cavities and the connecting passage, and can be partially removed from the lower element around the periphery of the second cavity so as to expose the connector for the purpose of calibrating or otherwise preparing the sensor for use with the two or more fluids without affecting significantly the sterility of the encapsulated elements, i.e. the sensing portion of the sensor and the cable.

BEST MODE FOR CARRYING OUT THE INVENTION

Generally, the present invention is a system for preparing a chemical sensor for use using two or more segregated fluids which are mixed at a selected time and even more generally is a unitary arrangement by which two or more fluids can be maintained segregated and then selectively mixed at a given time.

However, for purposes of illustration herein, the invention is described in the context of a particular chemical sensor, i.e. a pH sensor, and a particular application, i.e. calibration of the sensor at two operating points with the use of calibrating buffers (fluids) of two different values.

It should be understood that the principles of the present invention are not limited to pH sensors or calibration per se at two operating points nor is the invention limited per se to necessarily include only those applications for chemical sensors but conceivably could be used in other general mixing applications.

It should be further understood that the invention could include more than two vials and that the materials in the vials which are to be mixed could be liquids, gases or solid particulates, or combinations thereof.

Figure 1:
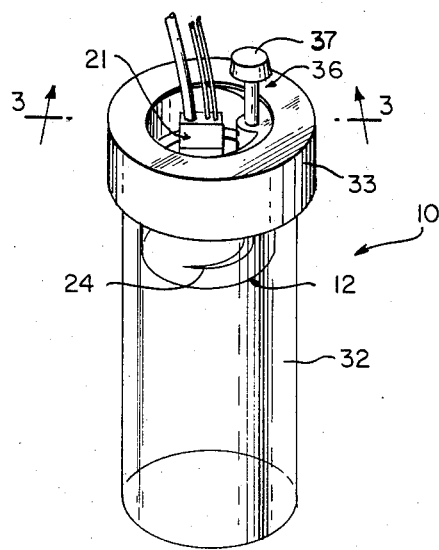
FIG. 1 is an environmental view of the article of the present invention.
Figure 2:
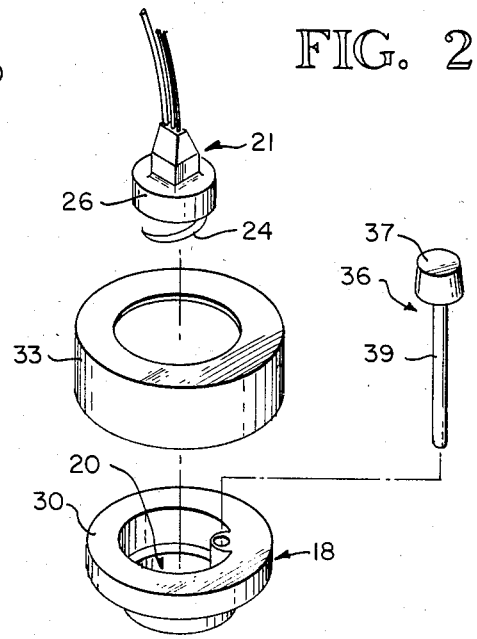
FIG. 2 is an exploded view of the article of FIG. 1.
Figure 3:
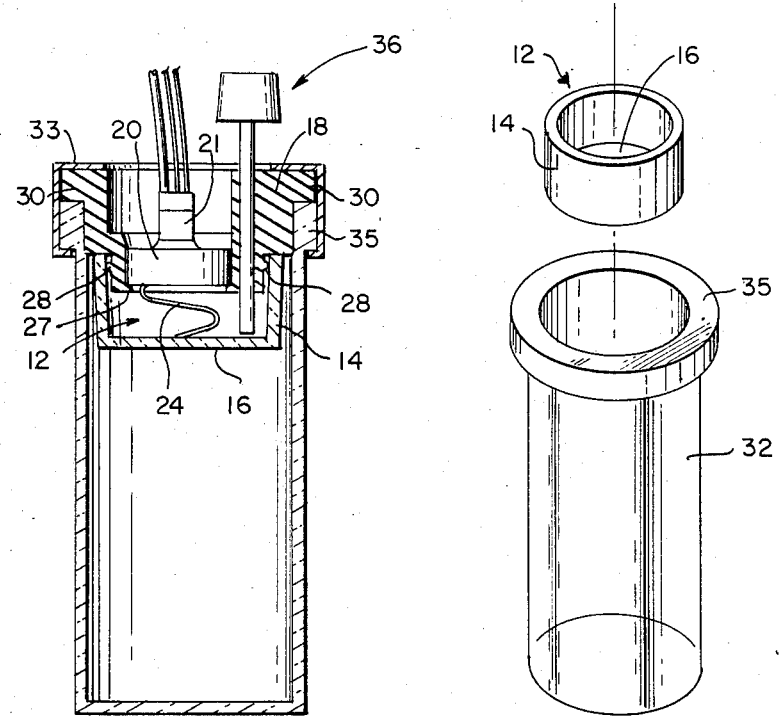
FIG. 3 is a cross-section view of the article of FIG. 1 taken along lines 3—3.

FIGS. 1-3 show an article of the present invention, generally at 10. The article includes a first cylindrical vial or cup 12 having a circular sidewall 14 and a bottom 16, but no top. In the particular embodiment shown, vial 12 is 0.34 inches deep with an inside diameter of 0.70 inches, with the sidewall 14 having a slight outward pitch, i.e. 2 degrees. Vial 12 is comprised of a clear plastic, such as Lexan 101 polycarbonate. The first vial 12, in the particular embodiment shown, is substantially filled with a calibrating buffer of a phosphate salt having a 7.00 pH. A colored dye can be added to the buffer if desired, for reasons explained hereinafter.

A stopper-like element 18 is configured to fit snugly into the top of vial 12, closing it off and sealing it, as shown most clearly in FIG. 3. Stopper 18 includes a central opening 20 which is configured to loosely receive the sensing portion 21 of the biomedical sensor, shown generally at 23. Typically, sensing portion 21 will include a needle-like element 24, frequently in the form of a spiral, which extends from a base 26.

The lower portion of the stopper 18 extends down into vial 12 and includes a peripheral rib 28 which contacts the inner surface of vial 12. The diameter of the rib 28 is slightly greater than the inner diameter of vial 12. Further, stopper 18 is made from a flexible, resilient, compressible elastomeric material, so that when the lower portion of the stopper is inserted in the vial 12, with the base 26 of sensing portion 21 in the opening 20 and the needle element 24 extending below the lower surface of the stopper, into the buffer, the stopper is compressed slightly against the side of base 26, tending to hold it firmly in place in the stopper. The lower edge of base 26 rests on a small peripheral lip 27 at the bottom of opening 20 in the stopper 18.

The upper edge portion of stopper 18 includes a upper circumferential lip 30 which extends out horizontally from the body of the stopper and mates with the upper peripheral edge of a second vial 32 in which the first vial is positioned. The upper lip 30 of stopper 18 rests on the top peripheral edge of vial 32, supporting the first vial 12 within the second vial 32. The second vial 32 in the embodiment shown is also cylindrical, having an interior depth of approximately 2.180 inches, and an interior diameter of approximately 0.900 inches. Vial 32 in the embodiment shown is a commercially available serum bottle made of clear glass, and is substantially filled with a calibration buffer having a pH of 7.40.

The pH value of 7.00 for the first calibration buffer and 7.40 for the second calibration buffer in the embodiment described were selected as the reasonable extremes of the physiological range of pH likely to be encountered in actual use of the sensor, i.e. the range of pH in human tissue. Both buffers use a standard phosphate salt in concentrations necessary to result in the desired pH values and the osmolarity required by the particular sensor being used.

The combination of first vial 12 and stopper 18 is held in place in the second vial by means of a conventional crimp ring 33. Crimp ring 32 is a thin aluminum ring which is configured to fit around the periphery of the upper lip 30 of stopper 18 and the upper lip 35 of vial 32. The ring 33 is crimped around the lower edge of lip 35 of vial 32, holding the stopper 18 fixedly to the second vial. The first vial 12, as described above, is releasably held to the stopper 18.

A plunger element 36 extends through a vertical opening in stopper 18. The plunger 36 comprises a cap element 37 in the form of a cylindrical section approximately 0.25 inches in diameter and an elongated pin-like element 39 which extends from the cap element 37. The cap element is above the upper surface of vessel 10, as shown in FIGS. 1 and 3, while the pin element extends down through the stopper to a point almost adjacent the lower surface of the first vial 12. While the pin element has a diameter relative to the opening therefore in the stopper 18 such that it is held in a given vertical position, the plunger can be easily pushed downwardly a short distance against the bottom of the first vial 12.

In operation of the article of FIGS. 1–3, the connector at the free end of the sensor cable is connected to a conventional calibrating apparatus (not shown). In the embodiment described herein, needle element 24 has been immersed continuously in the buffer in vial 12 and thus has been continuously hydrated during shipment and temporary storage.

The sensor is now ready for calibration, and it is first calibrated to the pH value of the first buffer, which in the example herein is pH 7.00. After the first calibration has been completed, plunger 36 is pressed downwardly, so that the bottom of pin element 39 presses vial 12 downwardly from contact with stopper 18. Vial 12 settles to the bottom of the second vial 32, so that the calibration buffer in the first vial mixes with the buffer in the second vial 32. The mixing of the two buffers in the embodiment shown results in a combined buffer having a pH value of 7.377. The dye in the first buffer (it could be in the second buffer as well, or both buffers) will also mix through the combined buffer, providing a visual indication that the two buffers have been combined. At this point, calibration of the sensor takes place with the combined buffer, and the sensor is ready to use.

A secondary effect of the vial 12 being released from the stopper is that the stopper slightly expands to its original diameter, which in turn results in a relaxation of the grip of the stopper on the base 26 of the sensing portion of the sensor. The sensor may now be easily removed from stopper 18, and is ready for use. Although the embodiment shown is useful for multiple calibrations, it can also be used for single calibrations, wherein the apparatus is used to releasably hold the sensor within the vessel.

Prior to actual use, it may be necessary to heat the sensor to a particular temperature, such as body temperature. The vessel 10 may be conveniently inserted into a heater configured to receive it (not shown). The heating typically will include a heating element which will heat the vessel 10 and the combined buffer therein and then the sensor itself. The vessel 10 can then be discarded.

As discussed above, it should be understood that a vessel could be used with more than 2 vials, so that several mixing steps would be possible, and hence that more than two different fluids could be used. Further, the term "fluid" can include gaseous elements, liquid elements or particulate elements, anything capable of being mixed together. The invention is described in the context of calibrating a chemical sensor, but it is also useful in other activities with sensors and also is useful in mixing applications where a sensor is not included.

Typically, in the embodiment shown, as used in calibration of a chemical sensor, the vessel 10, i.e. the combination of the first and second vials, the stopper, the plunger and the crimp ring, as well as the chemical sensor, must be maintained in a sterile condition until the sensor is ready to use. In particular, the sensing portion of the sensor and a significant portion of the sensor cable, i.e. at least 18 inches, must be sterile when used.

Figure 4:
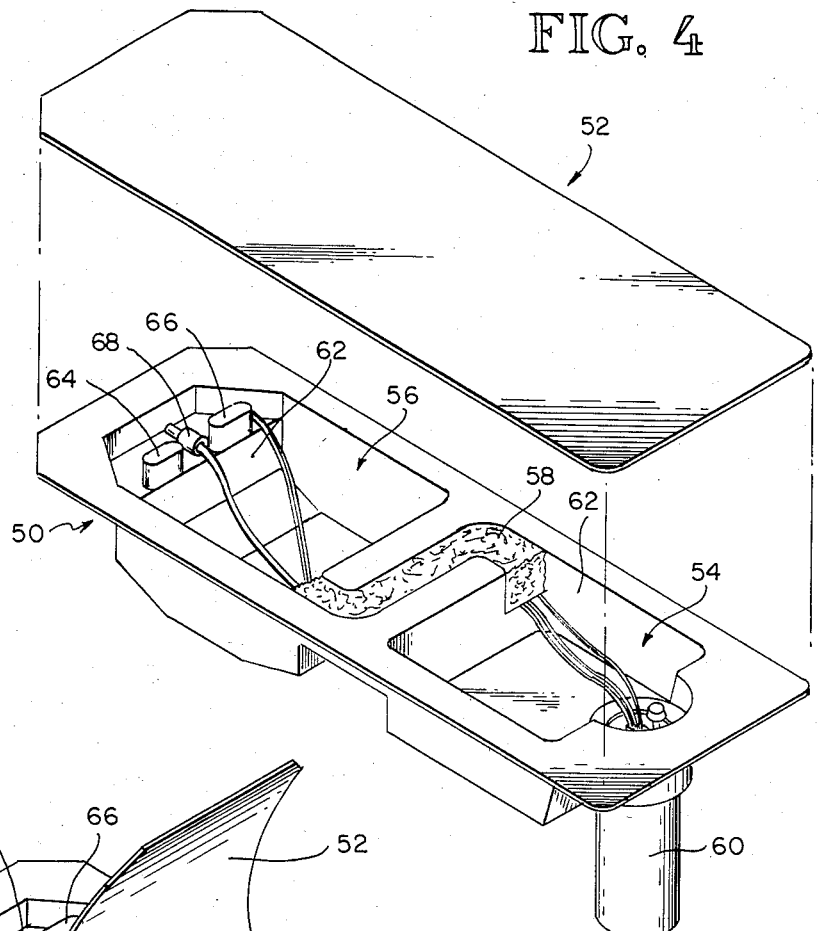
FIG. 4 is a partially exploded view showing the encapsulation of the article of FIG. 1.
Figure 5:
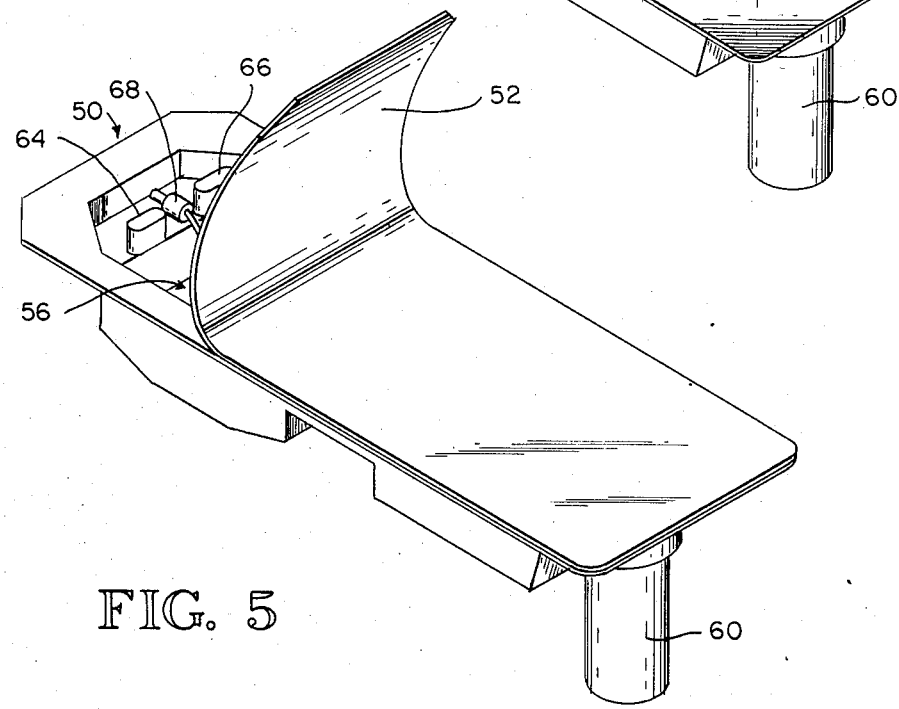
FIG. 5 is a view of the article of FIG. 4, showing the encapsulation partially removed.

FIGS. 4–5 show a sterile encapsulation package 50 in which the vessel 10, and the complete sensor, are first sterilized and then maintained in a sterile condition, through calibration and storage. The sterile encapsulation package 50 includes a lower package element 51 and an upper package element 52. In the embodiment shown the lower element is made from a stiff, clear plastic, approximately 0.03 inches thick, while the upper element is made from a very thin plastic or woven element such as Tyvek, a well-known material.

The lower element 51 includes first and second cavities 54 and 56 and a connecting passage 58. First cavity 54 includes a deep portion 60 which is configured to receive vessel 10 and the sensing portion of the sensor positioned therein, as shown in FIG. 4. The first cavity also includes an adjacent shallow portion 62 which is square in outline, approximately 2.6 inches on a side and approximately 1.0 inches deep, capable of receiving a substantial portion of the sensor cable extending from the sensing portion of the sensor.

The second cavity 56 is also shallow, approximately 2.75 inches on a side and approximately 1.25 inches deep at its lowest point. The second cavity includes a small raised portion 62 with two upstanding posts 64 and 66. The second cavity is adapted to receive the connector portion of the sensor and a small portion of the cable.

Connecting the first and second cavities is an S-shaped passageway 58. The passage 58 is approximately 0.4 inches wide and 0.56 inches deep. A portion of the sensor cable is positioned in this passageway. The passageway is otherwise filled with a cotton or foam material.

The top element 52 is a flexible sheet-like member which is heat sealed to the lower element 51 around the peripheries of the first and second cavities 54 and 56 and the passage 58.

With such an arrangement, vessel 10 and the chemical sensor therein can be sterilized, such as by an electron beam or gamma radiation, and then maintained in a sterile condition during shipment and storage thereafter, including calibration, until the sensor is ready for use. When the sensor is to be calibrated, the upper element 52 can be removed from the lower element around the periphery of the second cavity 56, so as to provide access to the connector 68. Such a partial removal of the element 52 permits calibration of the sensor without affecting the sterility of either the sensor probe or a substantial portion of the cable extending from the probe.

Following the first calibration, the plunger 36 can be depressed through upper element 52, so that the second calibration can be accomplished, without compromise of sterility. After the second calibration is completed, the upper member can be removed completely and the sensor removed from both the encapsulation package and the calibration vessel for immediate use.

Although a preferred embodiment has been described for purposes of illustration, it should be understood that various changes and modifications may be incorporated in such embodiment, as discussed above, without departing from the spirit of the invention, as defined by the claims which follow.

I claim:

1. An article for preparing a chemical sensor for use, comprising:
    a first vial containing a first preparing fluid having a first value;
    means for releasably holding said first vial, including means for releasably holding a portion of a sensor in said first vial, so that said portion can be exposed to the first fluid;
    a second vial containing a second preparing fluid having a second value;
    means for positioning said first vial within said second vial;
    means for releasing said first vial from said first vial holding means, thereby resulting in the mixing of said first and second fluids to form a combined fluid to which said portion of the sensor is exposed.

2. An article of claim 1, wherein said first and second preparing fluids are calibrating fluids.

3. An article of claim 2, wherein said calibrating fluids are liquids.

4. An article of claim 3, wherein the calibrating fluids are both pH calibrating buffers.

5. An article of claim 3, wherein at least one of the calibrating fluids contains a visible dye.

6. An apparatus of claim 3, wherein said releasing means is a pin-like plunger which extends through said stopper and which, when moved downwardly against the bottom surface of the first vial, releases the first vial from said stopper means, resulting in the mixing of the first and second calibrating fluids.

7. An article of claim 3, wherein the sensing portion of the sensor is held in the stopper in such a manner that the tip of the sensing portion is continuously hydrated by the first calibrating fluid.

8. An apparatus of claim 2, wherein said holding means includes a central opening to receive a sensing portion of the sensor and a peripheral lip for contact with the inner surface of said first vial, said holding means being in the form of a stopper comprising a compressible, resilient material, wherein the diameter of the lip is slightly greater than the interior diameter of said first vial so that as the stopper is inserted into said first vial, the stopper slightly compresses against the sensing portion of the sensor, tending to hold the probe portion in place when said first vial is in place, but permitting relatively easy removal of the sensor following the releasing of said first vial.

9. An apparatus of claim 1, wherein the volume of said first vial is approximately 0.12 cubic inches and the volume of said second vial is approximately 1.400 cubic inches.

10. An article of claim 1, including means for maintaining the sterility of the chemical sensor.

11. An article of claim 10, wherein said maintaining means includes means providing access to a connector portion of the sensor without disturbing the sterility of the sensing portion of the sensor and a substantial portion of the cable extending therefrom.

12. An article for preparing a chemical sensor for use, comprising:
    a first vial;
    means for releasably holding said first vial, including means for releasably holding a portion of a sensor in said first vial;
    a second vial;
    means for positioning said first vial within said second vial;
    means for releasing said first vial from said first vial holding means, wherein at least one of the first and second vials contain a fluid to which said portion of the sensor can be exposed for calibration thereof.

13. An article permitting selective mixing of two segregated elements, such as gases, liquids or particulates, comprising:
    a first vial containing a first element;
    means for releasably holding said first vial;
    a second vial containing a second element, wherein said second vial is positioned relative to said first vial and in said communication therewith that when said first vial is released, the first element is permitted to mix with said second element; and
    means for selectively releasing said first vial from said first vial holding means.

* * * * *